US010470836B2

(12) United States Patent
Yates

(10) Patent No.: US 10,470,836 B2
(45) Date of Patent: Nov. 12, 2019

(54) SKIN TENSIONER

(71) Applicant: Yates Hair Science Group, LLC, Chicago, IL (US)

(72) Inventor: William Yates, Vernon Hills, IL (US)

(73) Assignee: Yates Hair Science Group, LLC, Chicago, IL (US)

(*) Notice: Subject to any disclaimer, the term of this patent is extended or adjusted under 35 U.S.C. 154(b) by 245 days.

(21) Appl. No.: 15/549,128

(22) PCT Filed: Feb. 5, 2016

(86) PCT No.: PCT/US2016/016891
§ 371 (c)(1),
(2) Date: Aug. 4, 2017

(87) PCT Pub. No.: WO2016/127132
PCT Pub. Date: Aug. 11, 2016

(65) Prior Publication Data
US 2018/0243041 A1   Aug. 30, 2018

Related U.S. Application Data

(60) Provisional application No. 62/113,036, filed on Feb. 6, 2015.

(51) Int. Cl.
*A61B 90/00* (2016.01)
*A61B 17/00* (2006.01)
*A61B 17/02* (2006.01)

(52) U.S. Cl.
CPC .............. *A61B 90/02* (2016.02); *A61B 17/02* (2013.01); *A61B 2017/00752* (2013.01)

(58) Field of Classification Search
CPC ......... A61B 90/00; A61B 90/02; A61B 17/04; A61B 17/08
See application file for complete search history.

(56) References Cited

U.S. PATENT DOCUMENTS 5,611,811 A   3/1997 Goldberg
6,508,817 B1  1/2003 Pensler et al.
(Continued)

FOREIGN PATENT DOCUMENTS

FR        2758711 A1       7/1998
WO    WO 2014/042841 A1   3/2014
WO    WO 2016/127132 A1   8/2016

OTHER PUBLICATIONS

International Search Report and Written Opinion from International Application No. PCT/US2016/016891 dated Apr. 25, 2016, application now published as International Publication No. WO2016/127132 on Aug. 11, 2016.

*Primary Examiner* — Christopher J Beccia
(74) *Attorney, Agent, or Firm* — Morgan, Lewis & Bockius LLP

(57) ABSTRACT

A device for applying tension to a skin surface is provided. The device includes a first, second, third and fourth beam. Each of the beams has a main body, an extension extending from a first end of the main body and a second extension extending from a second end of the main body. The first end of the third and fourth beams have an opening defined therein and a slot sized to receive either the first extension of the first beam or the second extension of the first beam. The second end of the third and fourth beams have a slot sized to receive the other of the first extension of the second beam or the second extension of the second beam. The first extension of the first beam is slidably positioned within the slot on the first end of the third beam and the second extension of the first beam is slidably positioned within the slot on the first end of the fourth beam. The first extension of the second beam is slidably positioned within the slot on the second end of the third beam and the second extension of the second beam is slidably positioned within the slot on the second end of the fourth beam and the posts of the third (Continued)

and fourth beams extend through the openings on the extensions of the second beam.

17 Claims, 5 Drawing Sheets

(56) References Cited

U.S. PATENT DOCUMENTS

| | | |
|---|---|---|
| 6,585,746 B2 | 7/2003 | Gildenberg |
| 6,973,931 B1 | 12/2005 | King |
| 7,648,364 B2 | 1/2010 | Dauga et al. |
| 7,922,688 B2 | 4/2011 | Bodduluri et al. |
| 7,962,192 B2 | 6/2011 | Bodduluri et al. |
| 8,523,920 B2 | 9/2013 | Neev |
| 8,956,345 B2 | 2/2015 | Leonardi Kader |
| 2004/0049206 A1 | 3/2004 | Rassman |
| 2009/0110731 A1 | 4/2009 | Fritz et al. |
| 2010/0030260 A1 | 2/2010 | Fleischmann |
| 2012/0071794 A1 | 3/2012 | Karni |
| 2013/0282056 A1 | 10/2013 | Fleischmann |
| 2014/0074115 A1 | 3/2014 | Oostman, Jr. |
| 2014/0276959 A1 | 9/2014 | Oostman et al. |

SKIN TENSIONER

CROSS-REFERENCE TO RELATED APPLICATIONS

This application is a U.S. National Stage of International Patent Application No. PCT/US2016/016891, filed Feb. 5, 2016, which claims the benefit of priority to U.S. Provisional Application No. 62/113,036, filed Feb. 6, 2015, each of which is incorporated herein by reference in its entirety.

TECHNICAL FIELD

The present disclosure relates to devices for applying tension and stretching skin tissue on the scalp or other areas of the body for hair transplantation or other operations.

SUMMARY

According to one embodiment of the present disclosure, a skin tensioner is provided. The skin tensioner includes a first beam, a second beam, a third beam and a fourth beam. The first and second beams each have a main body. The main body of each of the first and second beams includes a first extension extending from a first end of the main body and a second extension extending from a second end of the main body. The first and second extensions of the first beam have a plurality of teeth defined thereon. The first and second extensions of the second beam have an opening defined therein.

The third and fourth beams each have a first end and a second end. The first end of the third and fourth beams each include an opening defined therein and a receiving slot sized to receive either the first extension of the first beam or the second extension of the first beam. The second end of the third and fourth beams each include a receiving slot sized to receive the other of the first extension of the second beam and the second extension of the second beam. Each of the third and fourth beam also include a post extending through the second receiving slot on the second end of the first and second extensions.

The first extension of the first beam is slidably positioned within the receiving slot on the first end of the third beam, and the second extension of the first beam is slidably positioned within the receiving slot on the first end of the fourth beam. The first extension of the second beam is slidably positioned within the receiving slot on the second end of the third beam, and the second extension of the second beam is slidably positioned within the receiving slot on the second end of the fourth beam. The posts of the third and fourth beams extend through the openings on the extensions of the second beam.

The tensioner also includes a first knob post having a first gear on a first end with teeth configured to cooperatively engage the teeth on the first extension of the first beam. The first knob post also includes a knob defined on a second end. The tensioner also includes a second knob post having a second gear on a first end having teeth configured to cooperatively engage the teeth on the second extension of the first beam. The second knob post also includes a knob defined on a second end. The first knob post extends through the opening in the first end of the third beam and the teeth of the first gear interact with the teeth on the first extension of the first beam. The second knob post extends through the opening in the first end of the fourth beam and the teeth of the second gear interact with the teeth on the second respective first and second extension of the first beam According to another embodiment of the present disclosure, a skin tensioner for applying tension to a skin surface is provided. The tensioner includes a first beam, a second beam, a third beam and a fourth beam. The first and second beams each have a main body. The main body of each of the first and second beams has a first extension extending from a first end of the main body and a second extension extending from a second end of the main body. Each of the first and second extensions of the second beam have an opening defined therein.

The third beam and a fourth beams each have a first end and a second end. The first end of the third and fourth beams each have an opening defined therein and a first receiving slot sized to receive either the first extension of the first beam or the second extension of the first beam. The second end of the third and fourth beam each have a second receiving slot sized to receive the other of the first extension of the second beam or the second extension of the second beam. Each of the third and fourth beam also include a post that extends through the second receiving slot on the second end.

The first extension of the first beam is slidably positioned within the receiving slot on the first end of the third beam and the second extension of the first beam is slidably positioned within the receiving slot on the first end of the fourth beam. The first extension of the second beam is slidably positioned within the receiving slot on the second end of the third beam, and the second extension of the second beam is slidably positioned within the receiving slot on the second end of the fourth beam. The posts of the third and fourth beams extend through the openings on the extensions of the second beam.

The device also includes an expandable screw having threaded extensions on opposing ends. The expandable screw is sized to be received by threaded openings in the third and fourth beams.

Other features of the tensioner disclosed herein will be apparent from the following disclosure taken in conjunction with the following drawings.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

Figure 1:
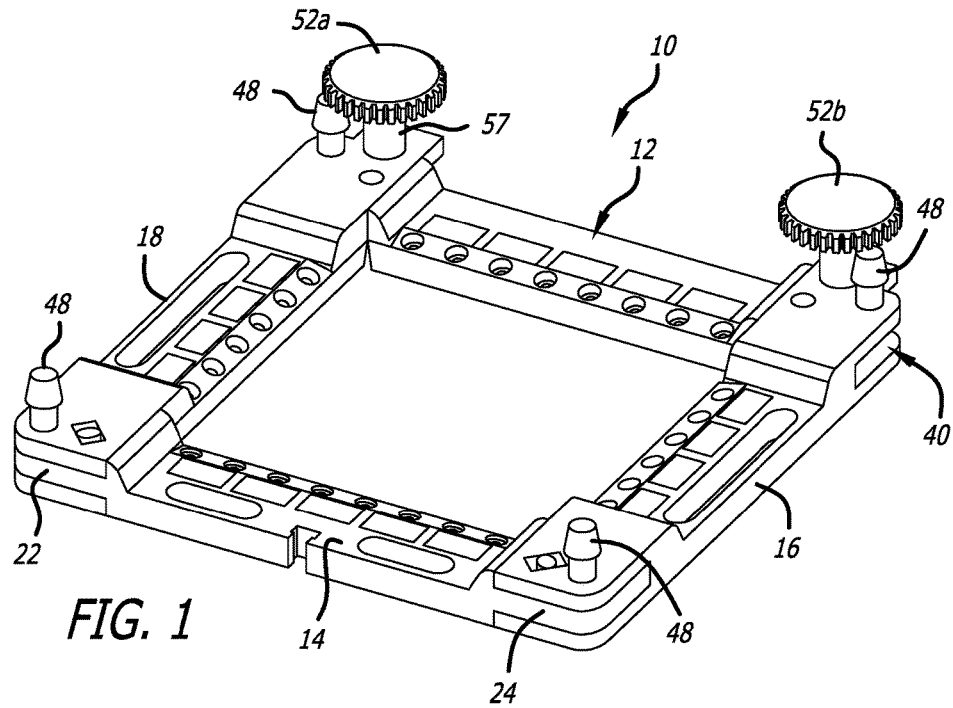
FIG. 1 is a top perspective view of a tensioner in a first position according to an embodiment of the present disclosure.

The components in the drawings are not necessarily to scale, emphasis instead being placed upon clearly illustrating the principles of the present invention.

DETAILED DESCRIPTION

While this disclosure is susceptible of embodiments in many different forms, there is shown in the drawings and will herein be described in detail preferred embodiments of the disclosure with the understanding that the present disclosure is to be considered as an exemplification of the principles of the disclosure and is not intended to limit the broad aspect of the disclosure to the embodiments illustrated.

Disclosed herein are various embodiments of a tensioner 10. Generally, tensioners are used to applying tension to the skin of a patient's scalp for purposes of hair transplantation or other operations. In one embodiment shown in FIGS. 1-4, The tensioner 10 includes four separate beams that interact with each other to apply tension to the skin. Accordingly, the tensioner 10 includes a first beam 12, a second beam 14, a third beam 16 and a fourth beam 18. The first beam 12 includes a main body 20. The main body 20 has a first extension 22 extending from a first end of the main body 20 and a second extension 24 extending from a second end of the main body 20. The first and second extensions 22, 24 extending from the main body 20 of the first beam 12 each include a plurality teeth 15 defined on or proximate at least one outer edge surface of the respective first and second extensions 22, 24. The first and second extensions 22, 24 extending from the main body 20 of the first beam 12 preferably have a thinner cross-section (as defined by the distance between an upper and lower surface of the extensions) than the cross-section of the main body 20 (as defined by the distance between an upper and lower surface of the main body 20) of the first beam 12.

Figure 2:
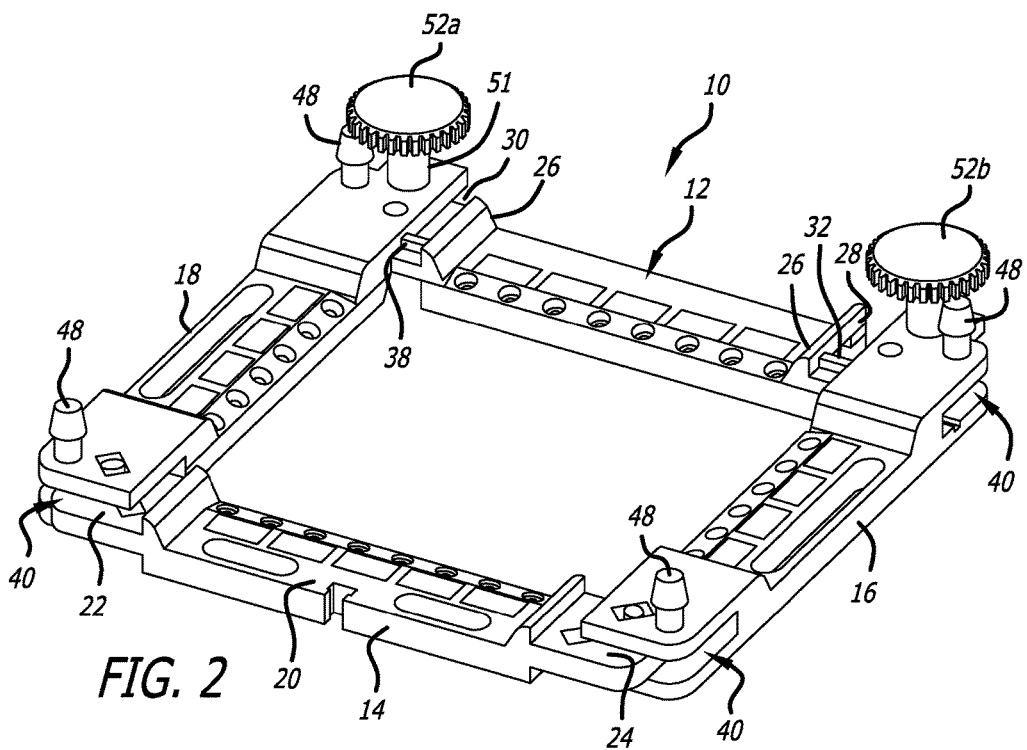
FIG. 2 is a top perspective view of the tensioner of FIG. 1 in a second position according to an embodiment of the present disclosure.
Figure 3:
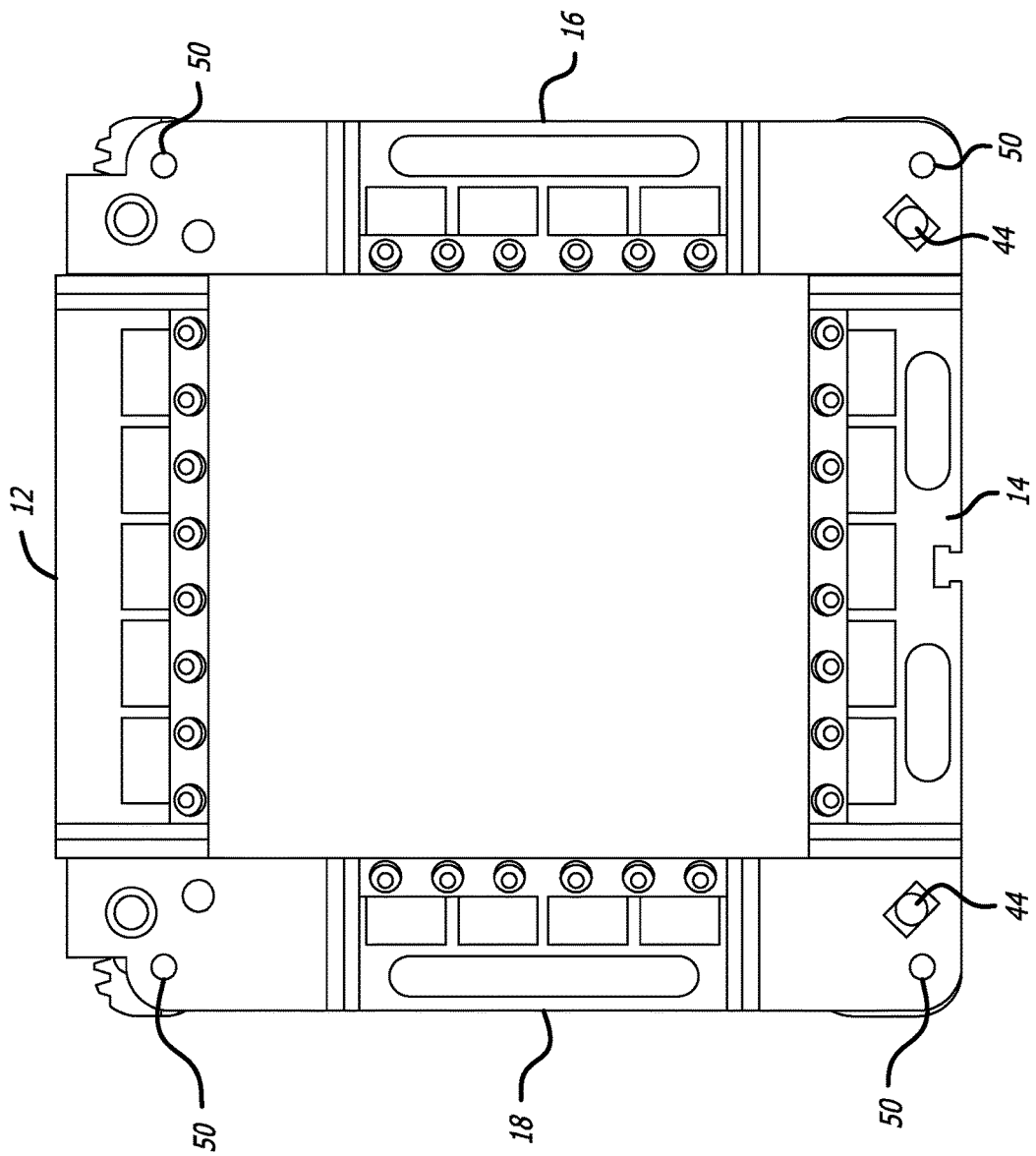
FIG. 3 is a bottom view of the tensioner in FIG. 1.

As shown in FIG. 2, the upper surface of the first beam 12 includes upstanding vertical stops 26 on the upper surface of the first beam 12. The vertical stops 26 are positioned proximate the first and second ends of the main body 20 of the first beam 12 proximate the transition of the main body 20 to the first extension 22 and the second extension 24, respectively. As illustrated in FIG. 2, the stops 26 are generally wedge-shaped and include a flat surface 28 that faces the first and second extensions 22, 24 of the beams 12, 14, 16, 18. It will be understood, however, that the stops 26 may take any shape suitable to prevent over-travel of the beams 12, 14, 16, 18 relative to one another.

Figure 4:
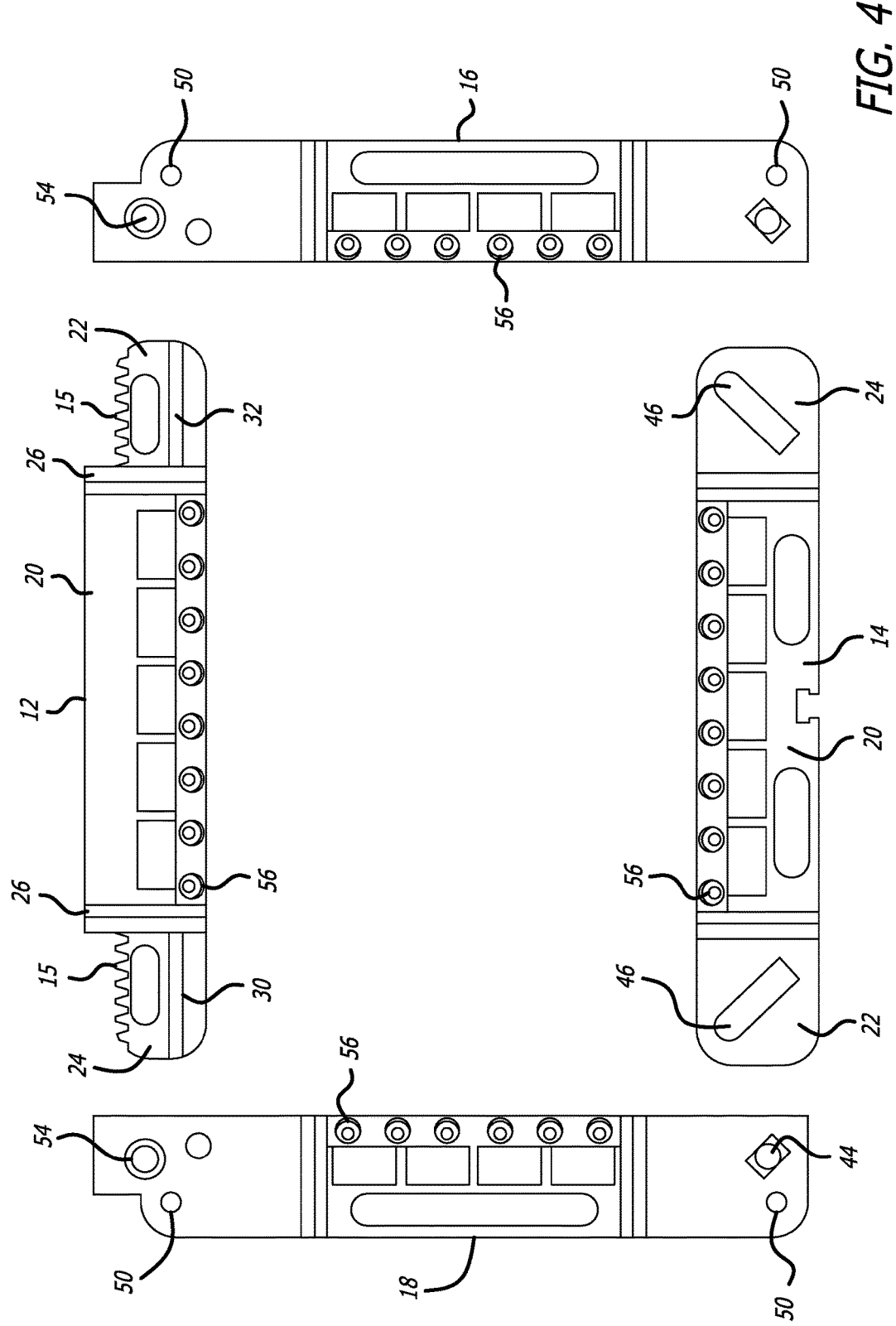
FIG. 4 is an exploded bottom view of the tensioner of FIG. 1.

As shown in FIG. 4, the first beam 12 can also include a first alignment flange 30 that is upwardly projecting (or upstanding) from the upper surface of the first extension 22, and a second alignment flange 32 that projects upwardly from the upper surface of the second extension 24. Although the alignment flanges 30, 32 are illustrated herein as having a generally rectangular cross-section, it will be readily apparent to those of skill in the art that the alignment flanges can be any shape suitable to facilitate structural alignment and the path of travel of the first beam 12 relative to the remaining beams.

The second beam also includes a main body 20 with a first extension extending from a first end of the main body and a second extension extending from a second end of the main body. The first and second extensions extending from the main body of the first beam each include an opening and preferably have a thinner cross-section (as defined by the distance between an upper and lower surface of the extensions) than the cross-section of the main body (as defined by the distance between an upper and lower surface of the main body) of the second beam. In one embodiment, shown in FIG. 4, the openings are disposed at an angle in relation to the sides of the second beam.

The upper surface of the second beam also may include upstanding vertical stops 26 on the top side of the second beam. The vertical stops 26 are positioned proximate the first and second ends of the main body 20 of the second beam proximate the transition of the main body 20 to the first extension and the second extension, respectively. Again, the stops 26 are generally wedge-shaped and include a flat surface that faces the extensions of the second beam. However, the stops 26 may take any shape suitable to prevent over-travel of the beams relative to one another.

The tensioner 10 also includes a third beam 16 and a fourth beam 18. The third beam 16 and the fourth beam 18 each include a first end. As shown in FIG. 1-4, the first end of each of the third and fourth beams 16, 18 includes a plurality of openings 36 defined therein and a receiving slots 40 sized to receive either the first extension of the first beam or the second extension of the first beam.

The first ends of the third and fourth beams 16, 18 include first and second alignment channels 38. The first and second alignment channels 38 are shaped to correspond to the shape of the first and second alignment flange of the first and second extensions of the first beam. The second ends of the third and fourth beams 16, 18 each include a receiving slot 40. The receiving slot 40 is sized to receive either the first extension 22 of the second beam 14 or the second extension 24 of the second beam 14.

In operation, the first alignment flange 30 of the first beam 12 is seated in the alignment channel 38 of the third beam 16. The second alignment flange 32 of the first beam 12 is seated in the alignment channel 38 of the third beam 16. The corresponding first and second alignment flanges 30, 32 on the second end of the first beam 12 are seated in the alignment channels 38 of the fourth beam 18. It will be understood that the alignment channels 38 may be lubricated with any lubricant known in the art to allow the flanges to slide freely within the alignment channels 38 when the tensioner 10 is operated. Furthermore, it will be understood that the channels 38 and flanges 30, 32 can take any cooperative shape. Moreover, it will be understood that the flanges 30, 32 may be positioned on the main body 20 of the second beam or on the extensions of the second beam 14. In an alternative embodiment, the positions of the channels 38 and flanges 30, 32 may be reversed such that the flanges 30, 32 are positioned on the third and fourth beams 16, 18 and the channels 38 are positioned on the second beam 14.

As shown in FIGS. 1 and 2, the first extension of the first beam is slidably positioned within the receiving slot 40 on the first end of the third beam 16. Similarly, the second extension 24 of the first beam 12 is slidably positioned within the receiving slot 40 on the first end of the fourth beam 18. The first extension 22 of the second beam 14 is slidably positioned within the receiving slot 40 on the second end of the third beam 16. The second extension 24 of the second beam 14 is slidably positioned within the receiving slot 40 on the second end of the fourth beam 18.

A post 44 extends through slots on the second end of each of the third beam 16 and the fourth beam 18. The posts 44 each are positioned in openings in the upper sections of slots 46 and extend down through the slots into openings on the bottom sections of the slots 46. The posts each have a width that is less than the width of the slots 46 in which they are positioned. Accordingly, the posts 44 can slide within the slots 46 yet still maintain stability of the structure. According to one embodiment, the length of the posts 44 is less than the length of the slots 46 thereby permitting the posts 44 to slide in within the slots 46.

In one embodiment, the third and fourth beams 16, 18 include threaded openings 50 in the respective second ends 35. The threaded openings 50 are sized to correspond to threaded locking pins 48 that, when threaded into the openings 50, extend into the receiving slots 40 on the second ends of the third and fourth beams 16, 18. This engagement acts as a locking mechanism to maintain the position of the beams when the beams are moved to a second position.

In one embodiment, the tensioner 10 includes a first knob post (not shown) that extends through the opening 54 in the first end of the third beam 16. The first knob post includes a first gear on a first end. The gear has teeth on an outer circumference. The teeth of the gear cooperatively mesh with the teeth 15 on the first extension 22 of the first beam 12. A knob 52a is defined on a second end of the knob post and is configured such that turning the knob 52a cause rotation of the first gear.

The tensioner 10 also includes a second knob post (not shown) that through the opening 54 in the first end of the fourth beam 18. The second knob post also has a second gear on a first end. The gear has teeth that cooperatively mesh with the teeth 15 on the second extension 24 of the first beam 12. A knob 52b is defined on a second end of the knob post and is configured such that turning the knob 52b cause rotation of the second gear.

All or any of the first, second, third and fourth beams 16, 18 each can include an array of small needles or pins on their bottom surface. It is contemplated that the pins can be permanently attached to the beams. Alternatively, the pins can be removably attached to a threaded screw that cooperative engages a corresponding threaded openings in the beams. Accordingly, the pins can replaced or removed when worn or otherwise necessary.

In operation, the tensioner 10 is positioned on an area of skin so that the pins 56 on the bottom side of the beams pierce the skin. Once the pins have pierced the skin, the operator turns the first and second knobs 52a, 52b. This, in turn, rotates the first and second gears respectively. The knobs 52a, 52b may be turned in unison, or one at a time. The interaction of the meshed teeth of the first gear and the first beam 12 causes the first end of the third beam 16 to move away from the first beam 12. At the second end of the third beam 16, the post slides within the angled slot 60 to move the second end of the third beam 16 away from the first end of the second beam 14.

The same process may be repeated with the second knob 52b and second gear to similarly move the first and second ends of the fourth beam 18 away from the second end of the first beam 12 and the second end of the second beam 14 respectively. This process moves the beams from a first position to an expanded second position. As the beams move from the first position to the second position, the pins 56 embedded in the skin stretch the skin out and put it in tension. Once the beams are in the second position, the threaded posts 44 on the second ends of the third and fourth beams 16, 18 can be extended into the slots to maintain the tensioner 10 in the second, expanded position. This process may also be automated in a robotic machine. Furthermore, the beams can be moved to more than just two positions, and the third and fourth beams 16, 18 do not necessarily have to be moved identical distances.

Figure 5:
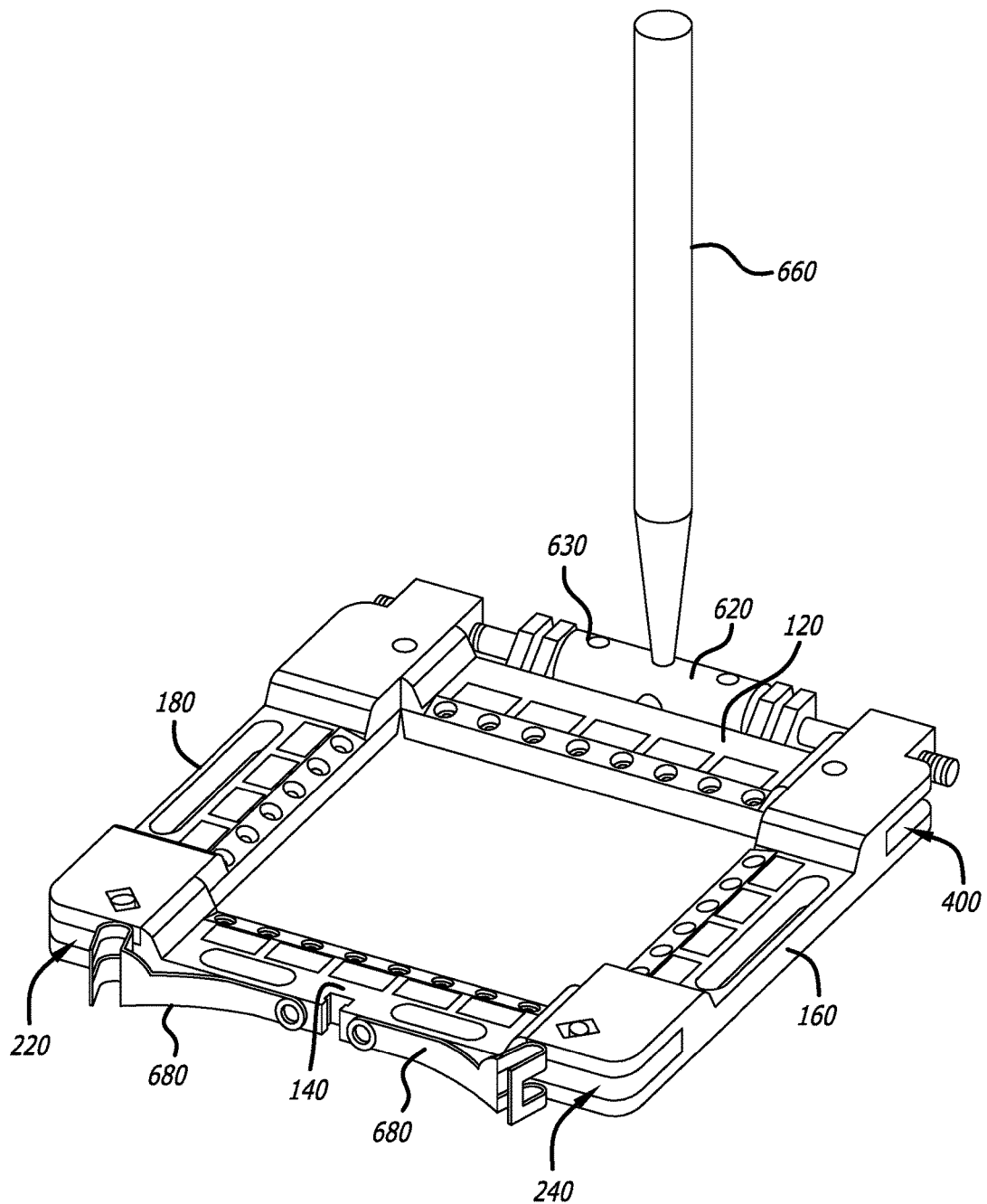
FIG. 5 is a top perspective view of a tensioner (with tool), wherein the tensioner is in a first position according to another embodiment of the present disclosure.
Figure 6:
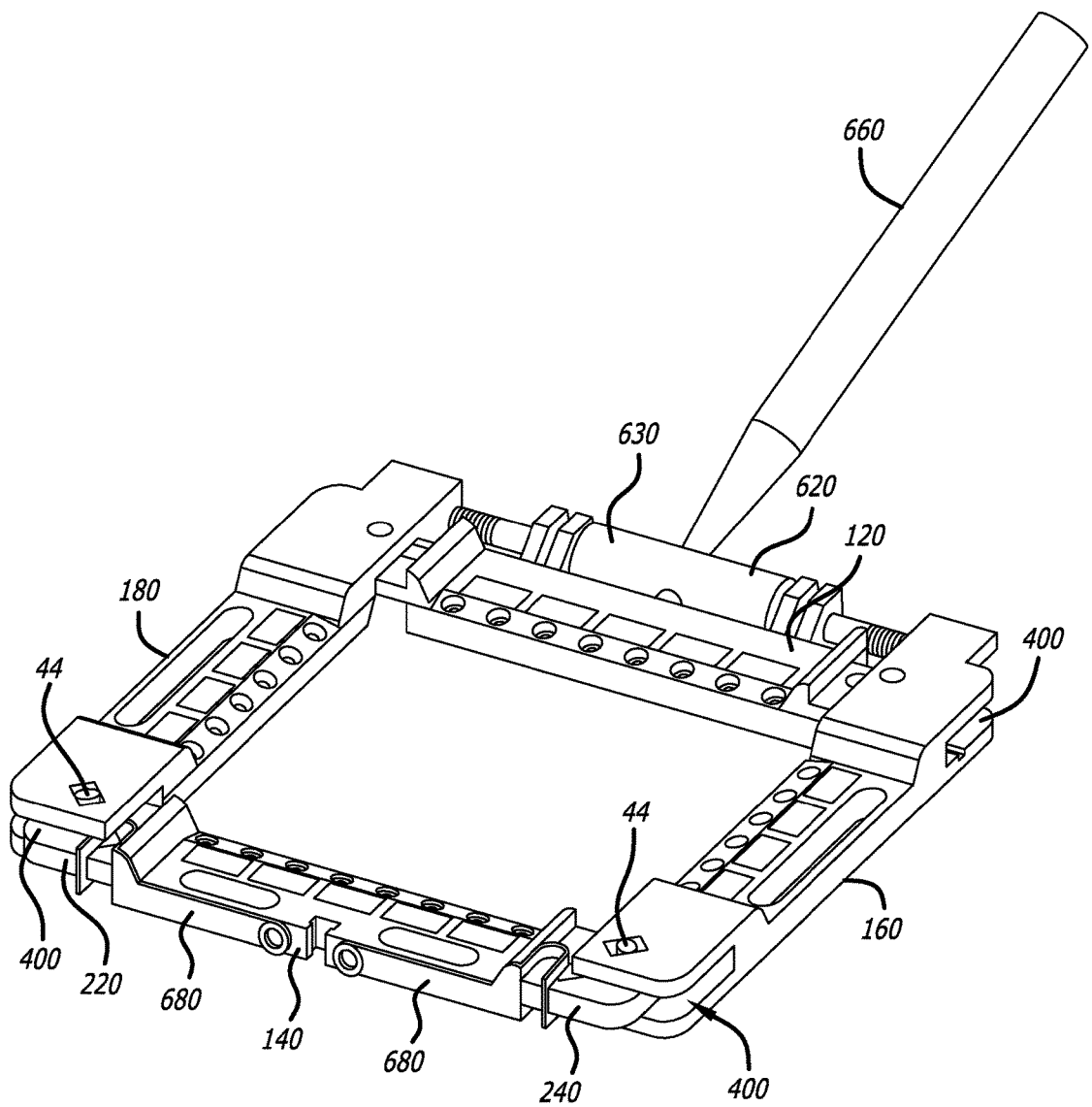
FIG. 6 is a top perspective view of the tensioner (with tool) of FIG. 5, wherein the tensioner is in a second position.

In another embodiment shown in FIGS. 5 and 6, the tensioner 100 includes a first beam 120, a second beam 140, a third beam 160 and a fourth beam 120, 140, 160, 180. The first and second beams 120, 140 each have a main body 200. The main body 200 of each of the first and second beams 120, 140 has a first extension 220 extending from a first end of the main body 200 and a second extension 240 extending from a second end of the main body 200. Each of the first and second extensions 220, 240 of the second beam 140 have an opening defined therein.

The third beam 160 and a fourth beams 180 each have a first end and a second end. The first end of the third and fourth beams 160, 180 each have an opening defined therein and a first receiving slot 400 sized to receive either the first extension 220 of the first beam 120 or the second extension 240 of the first beam 120. The second end of the third and fourth beam 160, 180 each have a second receiving slot 400 sized to receive the other of the first extension 220 of the second beam 140 or the second extension 240 of the second beam 140. Each of the third and fourth beam 160, 180 also include a post that extends through the second receiving slot 400 on the second end.

The first extension 220 of the first beam 120 is slidably positioned within the receiving slot 400 on the first end of the third beam 160 and the second extension 240 of the first beam 120 is slidably positioned within the receiving slot 400 on the first end of the fourth beam 180. The first extension 220 of the second beam 140 is slidably positioned within the receiving slot 400 on the second end of the third beam 160, and the second extension 240 of the second beam 140 is slidably positioned within the receiving slot 400 on the second end of the fourth beam 180. The posts of the third and fourth beams 160, 180 extend through the openings on the extensions of the second beam 140.

According to this embodiment, the tensioner includes an expandable screw 630 having threaded extensions on opposing ends. The expandable screw 630 is sized to be received by threaded openings in the third and fourth beams 160, 180. The expandable screw 630 is configured such that the length of the screw can be extended in opposed directions, thereby increasing the end-to-end length of the screw. In one embodiment, the expandable screw 630 includes a cylindrical center portion that may include one or more openings shaped to receive a tool 660. The tool 660 is inserted into one of the opening and levered to rotate the cylinder 620 thereby expanding the length of the expandable screw 630.

The third and fourth beams 160, 180 include threaded openings adapted to accept the threaded extensions of the expandable screw 630 and have second ends with slots 400 sized to receive either the first extension 220 of the second beam 140 or the second extension 240 of the second beam 140. The third and fourth beams 160, 180 further include posts extending through the receiving slots 400 on the second ends of the third and fourth beams 160, 180.

As previously discussed herein, an attachment may be provided to be disposed on the side of the second beam 140. The attachment has a first biasing member 680 (e.g., a leaf spring) disposed proximate a first and a second biasing member (e.g., a leaf spring) disposed proximate a second end. Once the beams are moved to the second position, the first leaf spring 680 snaps into place between the first vertical stop on the second beam 140 and the side of the third beam 160 and the second leaf spring 680 snaps into place in between the second vertical stop on the second beam 140 and the side of the fourth beam 180. This maintains the beams in the second position.

In operation, tensioner of this embodiment is positioned on an area of skin so that the pins on the bottom side of the beams pierce the skin. Once the pins have pierced the skin, an operator uses the tool 660 to turn the cylinder 620 on the expandable screw 630. The screw 630 expands thereby causing the first end of the third beam 160 to move away from the first beam 120. At the second end of the third beam 160, the post slides within the angled slot to move the second end of the third beam 160 away from the first end of second beam 140. The first and second ends of the fourth beam 180 similarly move away from the second end of the first beam 120 and the second end of the second beam 140 respectively. This method moves the beams from a first position to an expanded second position. As the beams move from the first position to the second position, the pins embedded in the skin stretch the skin out and put it in tension. Once the beams are in the second position, threaded posts on the second ends of the third and fourth beams 160, 180 can be extended into the receiving slots 400 to maintain the tensioner in the second, tensioned position. Alternatively, the leaf springs 680 can lock the tensioner into the second position. This process may also be automated in a robotic machine.

Furthermore, it is contemplated that the beams can be moved to any position between the first and second positions. In one embodiment, the beams can include ratchet mechanisms that allow the beams to lock at intermediate positions between the first and second positions. It is also understood that the third and fourth beams 160, 180 may be moved at differing distances through the use of different expandable screw 630.

The disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A device for applying tension to a skin surface, the device comprising:
   a first beam having a main body, a first extension extending from a first end of the main body and a second extension extending from a second end of the main body, each of the first and second extensions having a plurality of teeth defined thereon;
   a second beam having a main body, a first extension extending from a first end of the main body and a second extension extending from a second end of the main body, each of the first and second extensions having an opening defined therein;
   a third beam and a fourth beam, the third and fourth beams each having a first end and a second end, the first end of the third and fourth beams having an opening defined therein and a receiving slot sized to receive one of either the first extension of the first beam and the second extension of the first beam, the second end of the third and fourth beams having a receiving slot sized to receive the other of the first extension of the second beam and the second extension of the second beam, each of the third and fourth beam further comprising a post extending through the second receiving slot on the second end;
   wherein the first extension of the first beam is slidably positioned within the receiving slot on the first end of the third beam and the second extension of the first beam is slidably positioned within the receiving slot on the first end of the fourth beam, and the first extension of the second beam is slidably positioned within the receiving slot on the second end of the third beam and the second extension of the second beam is slidably positioned within the receiving slot on the second end of the fourth beam and the posts of the third and fourth beams extend through the openings on the extensions of the second beam;
   a first knob post having a first gear on a first end having teeth configured to cooperatively engage the teeth on the first extension of the first beam and a knob defined on a second end;
   a second knob post having a second gear on a first end having teeth configured to cooperatively engage the teeth on the second extension of the first beam and a knob defined on a second end; and
   wherein the first knob post extends through the opening in the first end of the third beam and the teeth of the first gear interact with the teeth on the first extension of the first beam, and wherein the second knob post extends through the opening in the first end of the fourth beam and the teeth of the second gear interact with the teeth on the second extension of the first beam.

2. The device of claim 1, further comprising a plurality of pins extending from a bottom side of the first and second beams.

3. The device of claim 1, further comprising a plurality of pins extending from a bottom side of the third and fourth beams.

4. The device of claim 1, wherein the first beam further comprises a first vertical stop defined on an upper surface of the first beam and a second vertical stop defined on the upper surface of the first beam.

5. The device of claim 1, further comprising a first alignment flange upstanding from an upper surface of the first extension, a second alignment flange upstanding from an upper surface of the second extension, a third alignment flange upstanding from a bottom surface of the first extension and a fourth alignment flange upstanding from a bottom surface of the second extension.

6. The device of claim 5, wherein the third beam further comprises a first alignment channel defined on an upper surface of the receiving slot on the first end of the third beam and the fourth beam further comprises a first alignment channel defined on an upper surface of the receiving slot on the first end of the fourth beam.

7. The device of claim 6, wherein the third beam further comprises a first alignment channel defined on a lower surface of the receiving slot on the first end of the third beam and the fourth beam further comprises a first alignment channel defined on a lower surface of the receiving slot on the first end of the fourth beam.

8. The device of claim 1, further comprising an opening on the second end of the third beam and an opening on the second end of the fourth beam, the openings each being threaded and sized to receive a threaded pin.

9. The device of claim 8, wherein when pins are threaded into the openings at the second ends of the third and fourth beams, the pins extend into the slots of the second ends of the third and fourth beams.

10. The device of claim 1, wherein when the first knob is rotated the third beam and second beam is moved from a first position to a second position, and when the second knob is rotated the fourth beam and the second beam move from a first position to a second position.

11. The device of claim 1, wherein the second beam further comprises a first vertical stop defined on an upper surface of the second beam and a second vertical stop defined on the upper surface of the second beam.

12. The device of claim 11, further comprising an attachment on a side of the second beam, the attachment having a first biasing member at a first and a second biasing member at a second end, said first biasing member biased to move into place between the first vertical stop on the second beam and the third beam and the second biasing member biased to move into place between the second vertical stop on the second beam and the fourth beam when the second beam is moved to the second position.

13. A device for applying tension to a skin surface, the device comprising:
a first beam having a main body, a first extension extending from a first end of the main body and a second extension extending from a second end of the main body; a second beam having a main body, a first extension extending from a first end of the main body and a second extension extending from a second end of the main body, each of the first and second extensions having an opening defined therein;
a third beam and a fourth beam, the third and fourth beams each comprising a first end and a second end, the first end having an opening defined therein and a first receiving slot sized to receive one of either the first extension of the first beam and the second extension of the first beam, the second end having a second receiving slot sized to receive the other of the first extension of the second beam or the second extension of the second beam, each of the third and fourth beam further comprising a post extending through the second receiving slot on the second end;
an expandable screw having threaded extensions on opposing ends, the expandable screw being sized to be received by a threaded openings in the third and fourth beams; and
wherein the first extension of the first beam is slidably positioned within the receiving slot on the first end of the third beam and the second extension of the first beam is slidably positioned within the receiving slot on the first end of the fourth beam, and wherein the first extension of the second beam is slidably positioned within the receiving slot on the second end of the third beam and the second extension of the second beam is slidably positioned within the receiving slot on the second end of the fourth beam and the posts of the third and fourth beams extend through the openings on the extensions of the second beam.

14. The device of claim 13, wherein the expandable screw further comprises a cylindrical center section, the cylindrical center section includes at least one opening defined thereon, wherein when the expandable screw is rotated the second beam, third beam and fourth beam move from a first position to a second position.

15. The device of claim 13, wherein the second beam further comprises a first vertical stop defined on an upper surface of the second beam and a second vertical stop defined on the upper surface of the second beam.

16. The device of claim 15, wherein the first vertical stop is defined on the upper surface of the first end of the main body of the second beam and before the first extension and the second vertical stop is defined on the upper surface of the second end of the main body of the second beam and before the second extension.

17. The device of claim 13, further comprising an attachment on a side of the second beam, the attachment having a first biasing member at a first and a second biasing member at a second end, said first biasing member biased to move into place between the first vertical stop on the second beam and the third beam and the second biasing member biased to move into place between the second vertical stop on the second beam and the fourth beam when the second beam is moved to the second position.

* * * * *